Jan. 4, 1927. Re. 16,515

F. M. BOWERS

HELMET AND MASK

Original Filed May 21, 1921 2 Sheets-Sheet 1

Inventor;
Frederick Mengle Bowers
By E. C. Brandenburg his Atty

Jan. 4, 1927. Re. 16,515

F. M. BOWERS

HELMET AND MASK

Original Filed May 21, 1921 2 Sheets-Sheet 2

Inventor;
Frederick Mangle Bowers
By E. C. Brandenburg
his Atty.

Reissued Jan. 4, 1927.

Re. 16,515

UNITED STATES PATENT OFFICE.

FREDERICK M. BOWERS, OF CHESTER, PENNSYLVANIA.

HELMET AND MASK.

Original No. 1,399,602, dated December 6, 1921, Serial No. 471,330, filed May 21, 1921. Application for reissue filed April 27, 1922. Serial No. 557,028.

The present invention relates to new and useful improvements in helmets and masks, and the construction herein disclosed is considered an improvement over that shown in Letters Patent of the United States numbered 1,135,759 granted to me April 13, 1915.

One of the objects of the invention is to so construct a headgear for masks that the latter is adjustable with respect to the head of the wearer.

Another object of the invention is to so construct a head gear that the same is universally adjustable in order that it may be used to support masks upon heads of various contour.

It is still a further object of the invention to provide a new and improved lens-holding device in masks of this character.

With the above and other objects in view, reference is had to the accompanying drawings in which—

Figure 1:
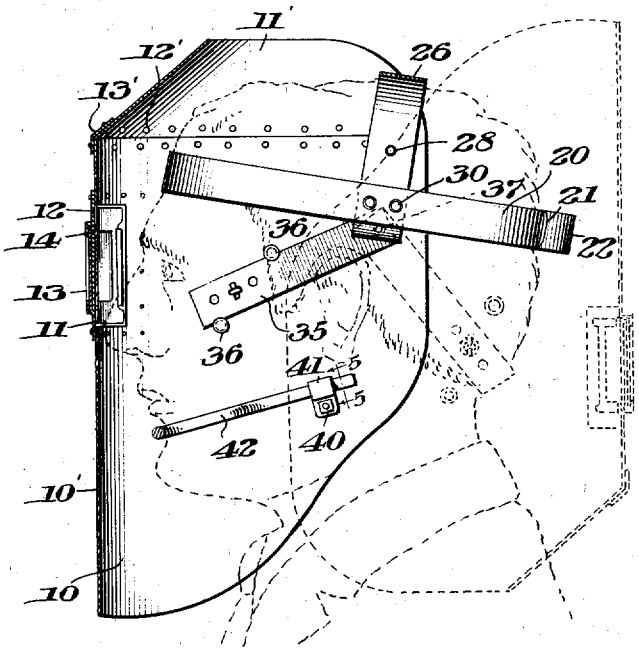
Figure 1 is a vertical sectional view of a mask constructed in accordance with the present invention and showing the method of applying the same to the head of the wearer.

Referring more particularly to the drawings, the reference character 10 designates the shield which is formed of any suitable heat-resisting material, such as fiber board, and said shield is cut out in its front portion as indicated by the reference character 11 to form a suitable sight opening in proper position to be in line with the eyes of the wearer.

The shield or mask 10 is formed from preferably two pieces of fiber board, there being one piece 10′ which forms the front portion of the mask and is adapted to occupy in normal operative position a vertical plane. Secured to the upper edge of that piece 10′, which forms the front of the mask, is a flange 11′, and said flange 11′ is secured to the upper edge of the piece 10′ by means of rivets or the like 12′. This joint between the two members 10′ and 11′ is further strengthened by means of a covering strip or bead 13′, said covering strip or bead being secured in position by means of the rivets 12′ heretofore mentioned. As shown in Fig. 1, the U-shaped member 11′ is made from a substantially flat strip of material and when bent into the U-shape and attached to the member 10′ at the meeting edges thereof, the member 11′ extends in a substantially straight line from the edge of the member 10′ to the top thereof at any transverse section throughout the length of said U-shaped member.

Figure 3:
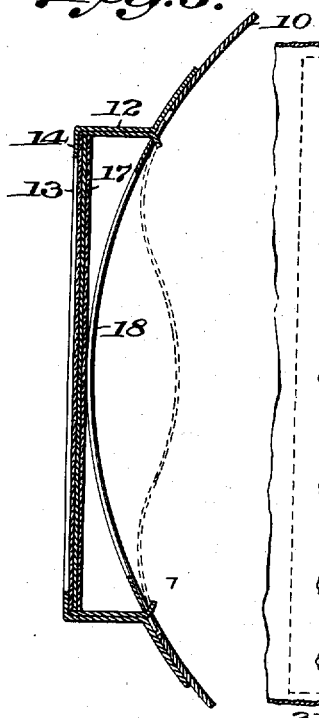
Fig. 3 is a horizontal sectional view taken through the lens holder.
Figure 4:
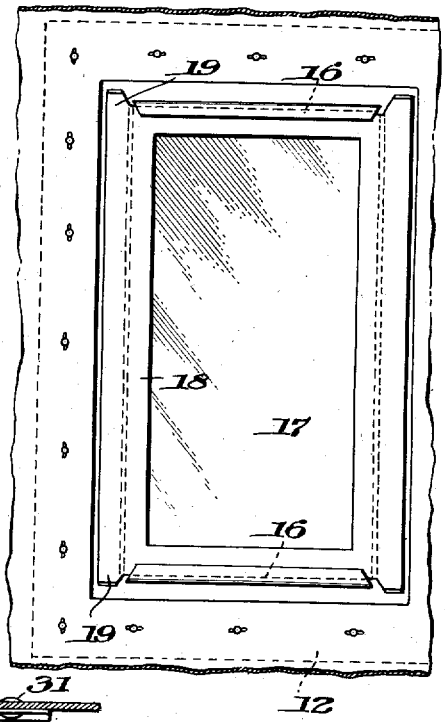
Fig. 4 is a view in elevation of the lens holder.
Figure 5:
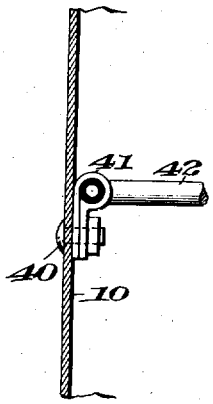
Fig. 5 is a detail sectional view taken on the line 5—5 of Fig. 1.
Figure 6:
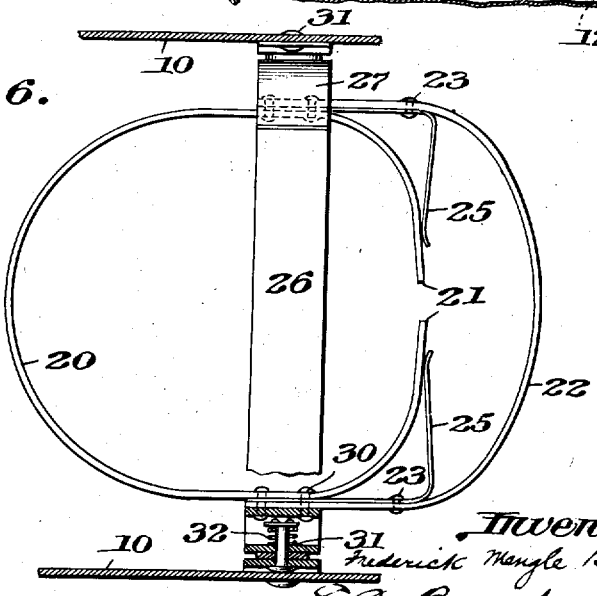
Fig. 6 is a top plan view of a slightly modified form of headgear.

Secured to the shield 10 at the cut-out portion 11, is a lens support or carrier 12. This lens support or carrier 12 has a sight opening 13, and the lens support is formed with a flange 14 upon its front face, which flange borders the sight opening 13. The lens holder 12 is preferably rectangular in shape and is provided at its opposite ends with inturned flanges 16. This lens holder is adapted to support a plurality of lenses 17, and in order to retain the lenses in position in the holder 12, a sheet metal frame 18 is employed. The frame 18 has its ends notched to form projecting legs 19, and the notched ends are adapted to engage beneath the flanges 16 heretofore mentioned. In Fig. 3 of the drawings is shown a method of positioning this lens retainer, and in this figure, after the lenses have been put in, the retainer or holder is moved from the dotted line position to the full-line position in said figure, where it engages the lenses at their front ends and retains them in position against the flange 14 heretofore mentioned. When the lenses are to be removed, the retainer 18 may be grasped and moved to the dotted-line position shown in Fig. 3 where the retainer is bodily removable after which the several lenses may be withdrawn as desired.

A suitable headgear for retaining the helmet in operative position is employed, and said headgear comprises a split band 20 adapted to encircle the head, said band being split as indicated by the reference character 21. Rigidly secured to the split band 20 and projecting rearwardly thereof is a substantially U-shaped member 22, and the rear end of said U-shaped member 22 is spaced with relation to the split portion of the band 20. Securely fastened to the U-shaped member 22, as at 23, and located upon each side of said U-shaped member 22, is a spring 24, and said spring 24 projects inwardly and engages the free ends of the split ring or band 20 as indicated by the reference character 25.

The reference character 26 designates a strap member and said strap member has its ends folded backwardly upon the body portion as indicated by the reference character 27, said ends being secured in position by means of rivets or the like 28. This strap member 26 is secured to the split band 20 and the U-shaped member 22 upon opposite sides thereof as indicated by the reference character 30, and the bent over ends 27 of this strap member form means for pivotally securing the headgear in position within the mask in the following manner: Upon opposite sides of the mask are located screws or rivets 31, and said screws or rivets form the means for pivotally mounting a rearwardly projecting bar 35, it being understood that there is one of these bars upon each side of the mask. Mounted upon opposite sides of the bar 35 are stops 36, and said stops 36 serve to limit the pivotal movement of said bar. As more clearly shown in Fig. 1, the bent-over ends 27 of the strap 26 are pivotally mounted to their respective bars 35, as indicated by the reference character 37, in order that a double pivotal movement may be had, said double pivotal movement being the pivotal movement of the bars 35 about their points of pivotal connection 31, and the pivotal movement of the headgear upon the rear end of the bars 35 about the pivotal point 37.

By this construction it is apparent that the mask may be swung upon these bent pivotal points to the position shown in dotted lines in Fig. 1, where it will rest at the back of the head of the wearer.

Figure 2:
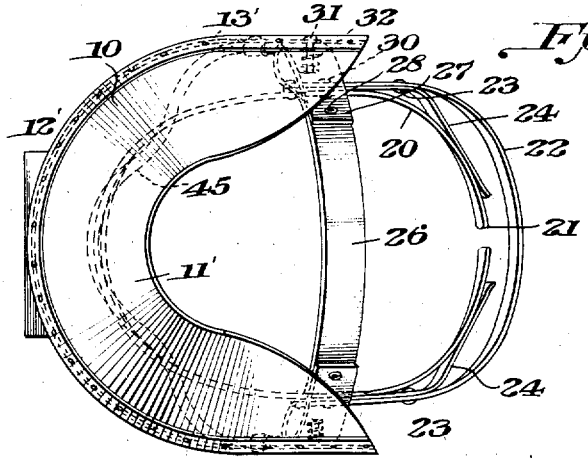
Fig. 2 is a top plan view thereof.

In Fig. 2 is shown a modified form of headgear in which the headgear is mounted by the strap 26, the turned-over ends of which are pivotally secured by bolts or rivets 31, to the opposite sides of the mask 10, and in order to increase the friction of the pivotal points, the spring 32 is interposed between the end of the bolts or rivet 31 and the bent-over end 27 of the strap 26.

Pivotally secured as at 40 to opposite sides of the mask are clips 41, and mounted in said clips 41, is a chin rest 42, positioned in such a manner that as the clips 41 are rocked about their pivotal point 40, the chin rest may be adjusted to the desired position to engage the chin of the wearer. As more clearly shown in Fig. 2 this chin rest is curved as indicated by the reference character 45 in order to conform to the shape of the chin of the wearer.

By this construction it will be seen that a new and improved form of mask is provided and that such mask may be constructed from separate pieces of relatively flat material which, when the several parts are secured together, they will, by reason of the manner in which they are secured, retain the necessary position to form the mask.

From the foregoing it is apparent that the present invention provides a new and novel headgear for masks of various kinds, which headgear owing to its method of securement to the mask permits of a movement of the mask from the position at the front of the head to a position at the rear of the head when it is not desired to use the mask.

In addition to the headgear, it is apparent that the present invention provides a new and novel form of lens holder, the use of which permits a ready removal and replacement of the lens.

I claim:

1. A mask including two main parts, one thereof being bent into substantially semicircular form, and the other member being approximately U-shape and being secured at its lower edge to the upper edge of the first-mentioned member at an obtuse angle thereto, said U-shape member extending in a substantially straight line at any transverse section throughout its length and having the extreme top and back portion thereof open.

2. A headgear for masks comprising a split band adapted to encircle the head, a U-shaped member embracing the split ends of said split band, resilient members interposed between the ends of the split band and the U-shaped member, and means for pivotally connecting said headgear within the mask.

3. A headgear for masks comprising a split band adapted to encircle the head, a U-shaped member enclosing the free ends of said split band, a plurality of resilient members interposed between the split band and the U-shaped member, a strap secured adjacent its ends to the split band, and means for pivotally mounting said headgear within the mask, said means being connected to the headgear at the ends of said strap.

4. A headgear for masks comprising a split head-encircling band, a U-shaped member encircling the split ends of said band, a spring interposed between each of the split ends of said head encircling band, and the U-shaped member said springs being carried by the U-shaped member, a strap extending over the head and connected adjacent its ends to the split band, and means pivotally carried by the ends of said strap for pivotally mounting the headgear within the mask.

5. A lens support having a flange upon its front face, a lens in position to rest against the flange, the lens support having inturned flanges, a frame having notched ends to engage the inturned flanges, and in position to hold the lens within the support.

6. A lens support having a flange upon its front face, a lens in position to rest against the flange, and a resilient bowed plate having a sight opening in the center thereof, and supported at its ends and adapted to engage the lens approximately midway therebetween.

In testimony whereof I affix my signature.

FREDERICK M. BOWERS.